(12) United States Patent
Dorn et al.

(10) Patent No.: US 7,553,322 B2
(45) Date of Patent: Jun. 30, 2009

(54) LUER CONNECTOR PORTION, AND STENT DELIVERY SYSTEM INCLUDING A CONNECTOR PORTION

(75) Inventors: Jürgen Dorn, Neulussheim (DE); Michael Vogel, Karlsruhe (DE)

(73) Assignee: C.R.Bard, Inc., Murray Hill, NJ (US)

( * ) Notice: Subject to any disclaimer, the term of this patent is extended or adjusted under 35 U.S.C. 154(b) by 997 days.

(21) Appl. No.: 10/481,351

(22) PCT Filed: Jun. 19, 2002

(86) PCT No.: PCT/EP02/06784

§ 371 (c)(1),
(2), (4) Date: May 11, 2004

(87) PCT Pub. No.: WO02/102279

PCT Pub. Date: Dec. 27, 2002

(65) Prior Publication Data

US 2004/0186547 A1    Sep. 23, 2004

(30) Foreign Application Priority Data

Jun. 19, 2001    (GB) .................................. 0114939.2

(51) Int. Cl.
*A61F 2/06*    (2006.01)
*A61M 29/00*    (2006.01)

(52) U.S. Cl. .................................................. 623/1.11
(58) Field of Classification Search ................ 623/1.11; 606/108

See application file for complete search history.

(56) References Cited

U.S. PATENT DOCUMENTS

| 5,049,128 | A |   | 9/1991 | Duquette |
| 5,228,452 | A |   | 7/1993 | Samson |
| 5,242,423 | A |   | 9/1993 | Goodsir |
| 5,312,363 | A |   | 5/1994 | Ryan et al. |
| 5,336,192 | A |   | 8/1994 | Palestrant |
| 5,906,619 | A |   | 5/1999 | Olson et al. |
| 6,077,295 | A | * | 6/2000 | Limon et al. ................ 623/1.11 |
| 6,083,194 | A |   | 7/2000 | Lopez |
| 6,695,862 | B2 | * | 2/2004 | Cox et al. .................... 606/191 |
| 6,773,446 | B1 | * | 8/2004 | Dwyer et al. ................ 606/191 |
| 2003/0167060 | A1 | * | 9/2003 | Buzzard et al. ............. 606/108 |

FOREIGN PATENT DOCUMENTS

| DE | 31 32 323 A1 | 4/1983 |
| DE | 44 20 142 A1 | 12/1995 |
| EP | 0 947 212 A2 | 10/1999 |
| WO | WO 01/34061 A1 | 5/2001 |

* cited by examiner

*Primary Examiner*—Vy Q Bui

(57) ABSTRACT

The present invention relates to a connector which comprises the male portion of a Luer connector, wherein the male portion is extended axially into a pressure pad having a pressure surface.

1 Claim, 3 Drawing Sheets

LUER CONNECTOR PORTION, AND STENT DELIVERY SYSTEM INCLUDING A CONNECTOR PORTION

FIELD OF THE INVENTION

This invention relates to a connector portion useful particularly, but not exclusively, as part of a device for passing fluid into an annular cavity between an inner elongate body and an outer elongate tubular body of a stent delivery system, and also relates to a stent delivery system making use of the same connector. In particular, but not exclusively, this invention relates to a connector which comprises the male portion of a Luer connector. Furthermore, it relates to a device having a housing with a distal end, a proximal end and an off-axis end, wherein the housing provides a seating at the distal end thereof for the proximal end of an outer elongate tubular body which extends distally from the housing along an axis of the housing extending between the proximal and the distal ends, and wherein the distal and off-axis ends define respective openings which are in fluid communication with each other, and wherein the proximal end has a lumen which enables an inner elongate body co-axially within the outer tubular body to extend from the housing both distally and proximally along the axis thereof. It relates as well to a stent delivery system using the above mentioned connector and device.

BACKGROUND ART

The deployment of stents at a stenting site within a human or animal body requires careful handling of the stent delivery system to be used for deploying the stent. Exact positioning of the stent at the site of the stenosis prior to and during deployment is essential. The accuracy with which the stent can be deployed with respect to the occlusion inside the body lumen, as well as the skills of the surgeon in controlling the stent delivery system, will have an impact on the outcome of the operation.

Normally, a guidewire is used, to advance a stent delivery system containing the stent to be deployed into the body to the site of the stenosis. Once the distal end of the delivery system has reached the stenting site and the stent to be released is correctly located, the stent is released. To deploy a self-expanding stent it is known to gradually withdraw an outer sheath (otherwise called sleeve) holding the stent in a radially compressed configuration and thereby allow the stent to radially expand and to anchor itself inside the body lumen. In commercially available delivery systems, the stent is prevented by an inner catheter from moving proximally with the sleeve as it retreats proximally, and is held in a radially compressed state by a co-axially disposed outer sheath or sleeve enclosing the stent and the inner catheter. The relative axial positions of the inner catheter and the outer sleeve are varied by manipulation of the delivery system.

Since the stent as well as the stenosis are not directly visible to the surgeon performing the operation, the stent deployment procedure requires a visualisation procedure, usually the injection of a radiopaque fluid, in order to visualise the location of the stent inside the body lumen. The fluid is injected into an annular cavity between the inner catheter and the outer sheath. The position of the stent as well as the location of the stenosis itself can then be monitored from outside the patient's body by using X-ray imaging machines showing the images of radiopaque marker rings on the distal end of the delivery system and a reduced intensity image corresponding to the constricted volume of radiopaque fluid through the occluded site. This allows the surgeon/radiologist to find the location of the stenosis and place the stent with sufficient accuracy.

During the course of the delivery procedure, the radially compressed stent is held axially at a fixed position by a pusher surface of the inner catheter, which typically abuts the proximal end of the stent inside the outer sheath of the delivery system. The proximal movement of the outer sheath to release the stent exerts a proximally directed force onto the stent which urges the stent to move in the same way. The surgeon has to counteract this tendency of the stent to move proximally by applying an adequate, distally-directed force onto the pusher element in order to off-set the opposing forces and to thereby keep the position of the stent fixed.

Typically, the stent is mounted into the delivery system at a manufacturing site. Then, the entire assembly is sterilised and air-tightly packed in a specially designed sealed enclosure. During sterilisation and packaging, there is always the risk that the co-axial components of the assembly might move so that the outer sheath may be displaced with respect to the inner catheter. Consequently, the position of the stent might be changed during these steps prior to its placement.

Therefore, it would be desirable to have a delivery system with a fluid injection port which is protected against inadvertent or premature movement of the outer sheath relative to the stent but is still simple to use and economical to manufacture.

SUMMARY OF THE INVENTION

It is therefore an object of the invention to provide a stent delivery system which is economical to manufacture and easy to use and enables the surgeon both to lock the position of the inner catheter with respect to the outer sleeve and to inject fluid into the annular cavity between the inner catheter and the outer sleeve.

This object has been achieved by a simplified delivery system using the same component both for locking the position of the inner catheter with respect to the outer sleeve and for injecting fluid such as radiopaque fluid into the cavity between the inner catheter and the outer sleeve.

A stent delivery system which achieves the above-mentioned object is described in independent claim 1. The locking mechanism is provided by means of a locking end release device which is defined in independent claim 1. The pressure pad being part of the locking and release device is defined in independent claim 1.

Further preferred embodiments of the present invention are described in dependent claims.

BRIEF DESCRIPTION OF THE DRAWINGS

The accompanying figures, referred to herein and constituting a part hereof, illustrate preferred embodiments of the present invention, and together with the description serve to explain the principles of the invention.

FIG. 1 shows a cross-sectional view of a device for passing fluid into an annular cavity 30 of a housing of the device (which takes the form of a T-piece 2) and also between an inner catheter 26 and an outer sleeve 28.

Figure 1:
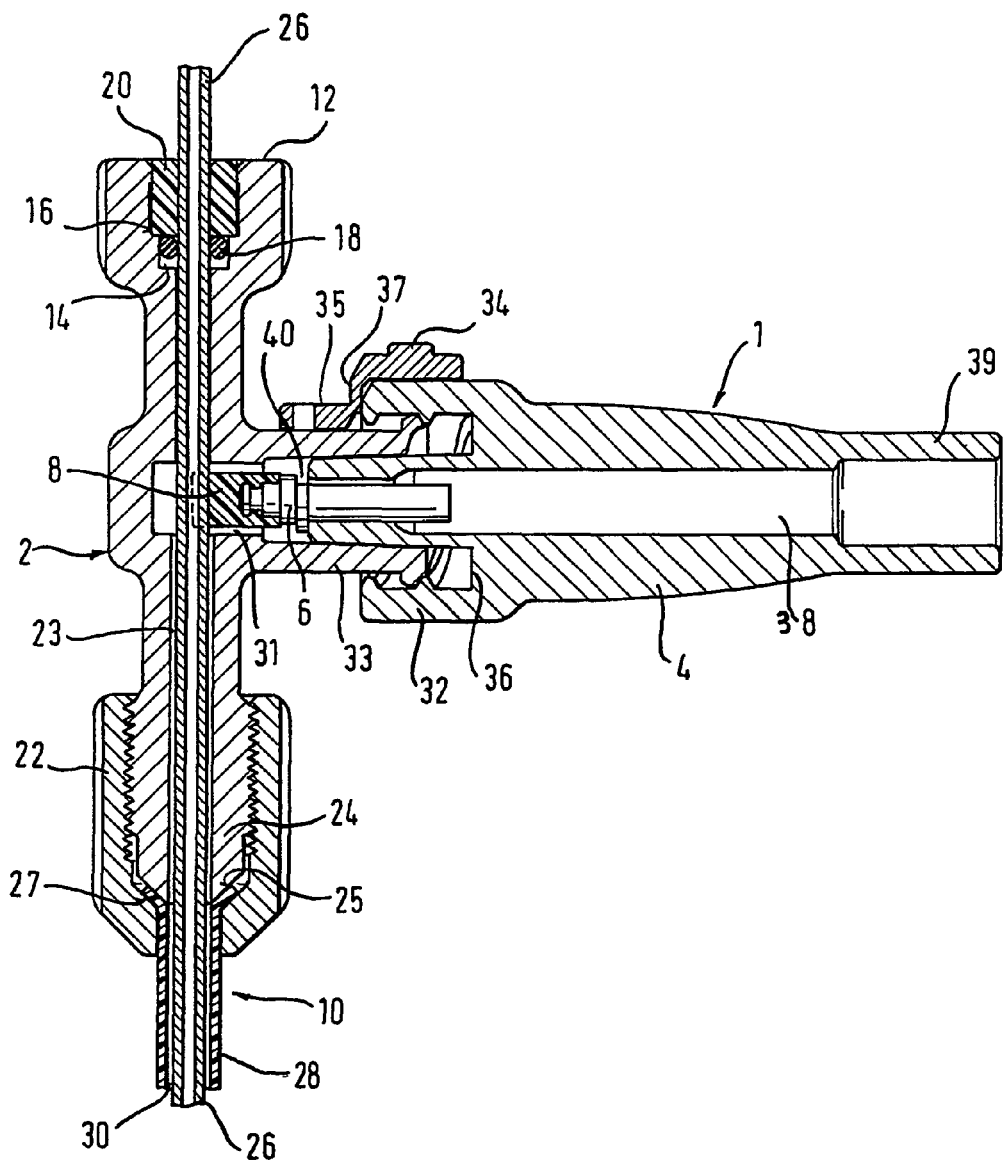
FIG. 1 shows in cross-section a device having a locking and release device attached thereto.

The device has a housing in the shape of a T-piece 2 comprising a distal end 24, a proximal end 12 and an off-axis end 36. A lumen 23 extends between the proximal and distal ends, and is in fluid communication with a lumen 31 in the side branch of the T-piece which leads to the off-axis end 36. It is the distal 24 and the proximal 12 end which define the axis of the device. The outer sleeve 28 of a stent delivery system is attached to the threaded distal end 24 of the device via a threaded female collar 22. The female collar 22 comprises a central through-hole through which the outer sleeve 28 is inserted and thermally clamped to the female collar 22. By "thermal clamping" is meant that the material of the proximal end of the outer sleeve 28 expands upon thermoforming heat treatment and retains its expanded shape when it returns back to ambient temperature. Hence, the radially-expanded proximal end of the outer sleeve 28 resists distal movement of the outer sleeve relative to the collar 22 when the process of thermal treatment is completed. It is also conceivable to use other means to attach the outer sleeve 28 to the distal end of the device, such as a press-fitting using re-entrant surfaces, or suitable adhesives. A seating 25 of the housing seals with a complementary seating 27 of the threaded collar 22.

The proximal end 12 of the device, as shown in FIG. 1, exhibits a recess having two different diameters whereby the innermost recess 14 in an axial direction accommodates an O-ring 18 for providing a fluid-tight seal with an inner catheter 26 and a plug 20 press-fitted into the larger diameter recess 16 in order to prevent the O-ring from slipping out of the smaller recess upon proximal movement of the inner catheter 26. It is also conceivable to screw the plug into the larger diameter recess or use an appropriate adhesive. Differently sized O-rings can be used to accommodate differently sized inner catheters for differently sized stents. This further enhances the versatility of the device.

The off-axis end 36 of the device shows a female Luer-lock element 33 which connects to a male Luer-lock assembly 32 thereby to serve as the locking and release device 1. Thus, the locking and release device 1 may also be recognised to be based on a Luer-lock connector. It comprises a passage 38 therethrough for passing fluid down the inner bore of the Luer connector. The inner end of the male Luer connector 32, which extends into the off-axis end of the T-piece 2, comprises a spigot 6 which is co-axial with, and located within, the internal bore 38 of the Luer connector. The spigot 6 is fixed inside the bore 38 of the Luer connector by means of an annular cutting edge which cuts itself into the material of the Luer connector (in the manner of a self-tapping screw) and thereby fixedly fastens the spigot 6 to the Luer connector 1. It is also conceivable to screw or press-fit the spigot into the Luer connector. The spigot 6 comprises a cut-out portion 40 at the end extending into the T-piece for providing a continuous passage for the fluid to be injected that is to say, fluid communication between the bore 38 and the lumen 23. The lower (in FIG. 1) end of the spigot 6 comprises re-entrant surfaces onto which an elastically deformable elongate locking member 8 is attached. The locking member 8 is made out of silicone rubber but other materials can be used. The end surface of the locking member 8, remote from the spigot 6, constitutes a pressure pad which bears on the inner catheter 26 when the locking member is in its locking disposition, as explained below.

A distinct feature of the Luer connector is its quick and easy installation, since it requires only less than half a turn to fully engage the male Luer-lock connector 32 with the female portion 33 of the mating Luer-lock on the off-axis side branch of the T-piece. The dimensions of the spigot 6 and the pressure pad 8 are such that, when bringing the male Luer-lock connector 32 into full engagement with the female element 33, the deformable locking member 8 extends sufficiently far enough beyond the end of the Luer-lock connector so that it experiences a compressive force due to pressing down onto the inner catheter 26. This means that, in the absence of the inner catheter 26, the elastic member intersects the locus or line of presence of the inner catheter, so that it undergoes deformation when such inner body is present. It is this compression of the locking member which prevents axial sliding movement of the inner catheter within the device. In this locking disposition, fluid can still be injected through the Luer-lock connector down into the T-piece lumen 23 and thereafter the annular cavity 30 between the inner catheter 26 and the outer sleeve 28. For ease of use, a syringe can easily be attached to the upper end 39 of the male Luer-lock element 32, that is, the end opposite the one being connected to the T-piece of the Luer connector via a Luer-lock connection, which upper end 39 for this purpose can exhibit the characteristic cone angle of a female Luer-lock portion.

The Luer connector optionally comprises a safety catch which prevents inadvertent release of the male Luer connector 32 from the T-piece 2. The safety catch illustrated comprises two portions, namely a portion 34 located on the male Luer connector 32 and preferably glued thereon and a portion 35 on the female Luer portion 33 and preferably glued to it. Between the portions 34, 35 is a frangible neck 37, which prevents rotation of the Luer connector until it is broken by relative rotation of the male and female Luer-lock portions. To release the safety catch, the Luer connector is rotated counter-clockwise thereby breaking the frangible neck 37. The safety catch is conveniently made of polymeric material. It is also conceivable to bring a pawl into engagement with a spring-biased toothed annulus on the housing 2 close to the off-axis end of the T-piece. To disengage the safety catch, the spring-biased toothed annulus is pushed towards the T-piece, thereby releasing the pawl and disengaging the Luer connector. Also, a shear pin for blocking the rotation of the Luer connector until it is broken in shear, or any other conventional locking mechanism that is suitable in size and weight can be used.

The entire structure is conveniently made out of synthetic polymeric materials.

Figure 2:
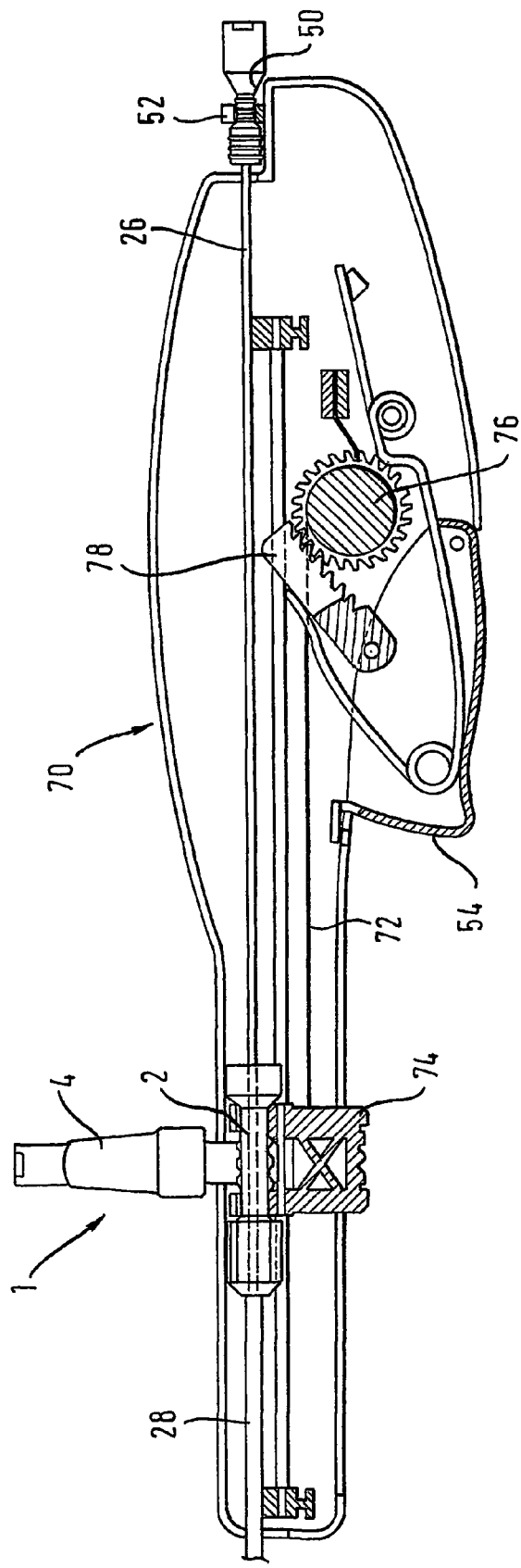
FIG. 2 is a longitudinal section through a stent delivery system using the locking and release device of FIG. 1.

FIG. 2 shows a perspective view of a stent delivery system using the locking and release device as well as the T-piece of FIG. 1 in an assembled state. The delivery system 70 is based on a trigger-principle for the proximal withdrawal of the outer sleeve with respect to the inner catheter. It is described in more detail in an international patent application No. PCT/EP02/04727, soon to be published, and hereby incorporated by this reference into the present disclosure. The proximal and distal end of the T-piece connector are engaged with mating parts of the delivery system, whereby the proximal end 50 of the inner catheter 26 is fixed in position by a mount 52 at the rear side of the trigger device. Upon actuation of the delivery system the T-piece is drawn rearwardly by a tension wire 72 and carriage 74, with successive squeezes of a trigger 54, that reel in the wire 72 on a capstan drum 76 which the trigger rotates through a rack 78. The carriage 74 carries the Luer-lock housing 2 towards the rear mount 52 step-wise, with each squeeze of the trigger 54, and thereby withdraws the outer sheath 28 to gradually release the stent.

During insertion of the stent into the delivery system, sterilisation and transport, the Luer-lock connector remains in its locking disposition, thereby preventing inadvertent sliding movement of the inner catheter with respect to the outer sleeve. It is only shortly before deploying the stent into the body lumen, that the Luer-lock connector 1 is disengaged from the T-piece 2. Once the stent has been properly placed at the site of the stenosis, the surgeon uses the trigger mechanism in order to proximally withdraw the outer sleeve and to release the stent. In case the surgeon has to temporarily interrupt the procedure of stent placement, the Luer-lock connector can be inserted back into the T-piece in order to fix the position of the inner catheter with respect to the outer sleeve.

Figure 3:
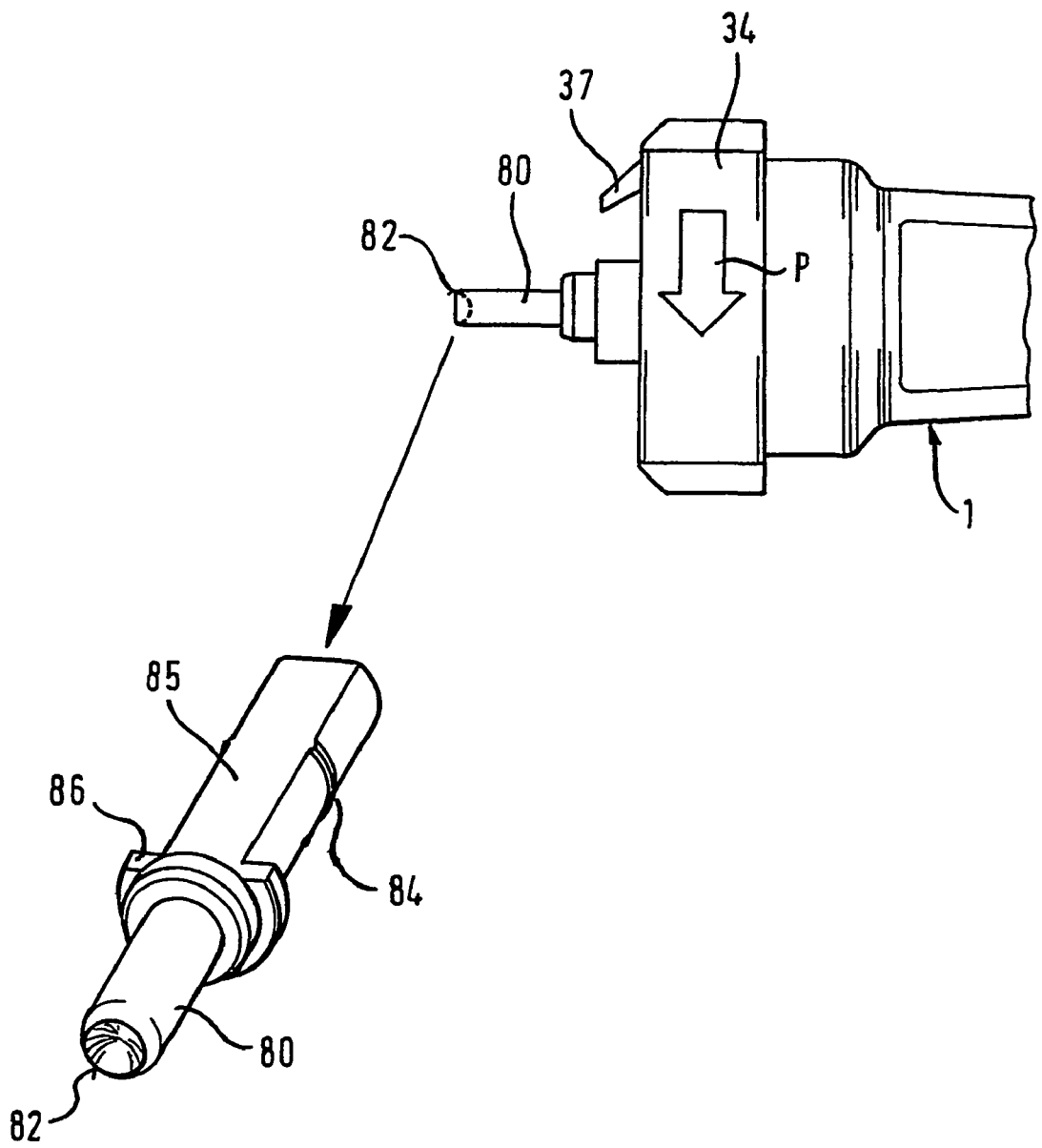
FIG. 3 shows in cross-section another embodiment of the locking and release device.

FIG. 3 shows in cross-section another embodiment of the locking and release device 1 in FIG. 1. It connects to the female Luer-lock element 33 at the off-axis end 36 of the device shown in FIG. 1 and comprises a passage therethrough (not shown) for passing fluid down the inner bore of the Luer connector 1, into lumen 23 of the T-piece connector 2.

The inner end of the locking and release device 1 which extends into the off-axis end of the T-piece 2 comprises a metal pin 80 which is co-axial with, and located within, the internal bore (not shown) of the Luer connector. The metal pin 80 is fixed inside the bore of the Luer connector by means of a press-fit. The end of the metal pin extending into the off-axis end of the T-piece is domed. The end surface of metal pin curves radially inwardly, uniformly from all radial directions. This dome-shape of the axial end of metal pin 80 effects line contact the annular edge 82 of metal pin 80 with the inner catheter 26. The dome-shaped end of metal pin 80 is also more clearly shown in the blown-up part of FIG. 3.

For providing fluid communication between the inner bore of the Luer connector 1 and lumen 23 of T-piece 2, the upper portion of metal pin in FIG. 3 to be inserted into the off-axis end of T-piece is oblate. When the metal pin is inserted into the male Luer connector, a gap remains between the oblated portion 85 of metal pin and the end portion of the Luer connector defining the inner bore. This way, fluid connection between inner bore 38 of Luer connector 1 and inner lumen 23 of T-piece is established.

The press-fit of metal pin into male Luer connector is ensured by the chamfered portion 84 of metal pin. A flange 86 serving as a stopper is provided on the metal pin. The flange also takes up any compressive stresses caused by the pushing of the pin onto the inner catheter.

To prevent inadvertent rotation of the male Luer-lock connector 1 with respect to the T-piece, an integrally moulded element is both attached to the Luer connector and the off-axis end of the T-piece. This element comprises portion 34, which circumferentially surrounds the near end of the Luer connector to the off-axis end of the T-piece, a frangible portion 37 and portion 35 circumferentially surrounding a section of the off-axis end of the T-piece. Arrows are provided on portion 34 indicating the medical practitioner what direction to turn the Luer connector in order to release it from the T-piece.

Upon rotation of the Luer male connector 1, frangible portion 37 breaks off portion 35, thereby allowing the Luer connector to be detached from the T-piece. The frangible portion 37 is designed such that it resists inadvertent rotation of the Luer connector prior to use of the Luer connector/T-piece assembly. It also serves as an indicator for the surgeon to indicate that the device shown in FIG. 1 has not been previously used in a surgical procedure, and sterility is still maintained.

The circular edge 82 of dome-shaped end of metal pin 80, in an assembled state of the device shown in FIG. 1, bites on the inner catheter 26 and prevents distal or proximal movement of the inner catheter with respect to the T-piece. The inventor of the present application have found that it is the sharp edge of metal pin 80 that effectively prevents this movement of the inner catheter. Preferably, the diameter of the 360° circular edge equals the diameter of the inner catheter 26. It is also contemplated that the material used for the metal pin should be harder than the material used for the inner catheter.

Although the illustrated embodiment shows a single T-piece being used for both introduction of radiopaque marker fluid and for clamping the inner catheter relative to the outer sheath, and although this is a useful advantage of the invention, nevertheless it will be appreciated that separate T-pieces could be used for these two separate functions. The advantage delivered by this invention, namely reliable and economical inner catheter clamping remains, even if radiopaque fluid is delivered elsewhere.

The invention claimed is:

1. A stent delivery system comprising:
an inner elongate body and an outer elongate tubular body which are co-axially arranged,
a pull-back device enabling proximal displacement of the outer body with respect to the inner body for releasing a stent contained within an annular cavity formed between the inner and outer body, into a body lumen,
a device for passing fluid into the annular cavity having a housing with a distal end, a proximal end and an off-axis end, the housing provides a seating at the distal end thereof for the outer elongate tubular body along an axis of the housing extending between the proximal and the distal end, the distal and off-axis ends defining respective openings which are in fluid communication with each other, and the proximal end having a lumen to enable the inner elongate body to extend from the housing both distally and proximally, along the axis thereof,
the stent delivery system being characterized by a locking and release device mounted to the housing and extending into the off-axis opening of the housing to bear, in a locking disposition, against the inner body to prevent axial movement thereof with respect to the outer body, and to simultaneously allow injection of fluid into the annular cavity and, in a released disposition, to be spaced from the inner body to permit axial movement of the inner body with respect to the outer body.

* * * * *